(12) United States Patent
Suhami et al.

(10) Patent No.: US 9,036,844 B1
(45) Date of Patent: May 19, 2015

(54) HEARING DEVICES BASED ON THE PLASTICITY OF THE BRAIN

(71) Applicants: Avraham Suhami, Petah Tikva (IL); Shmuel Suhami, Petah Tikva (IL)

(72) Inventors: Avraham Suhami, Petah Tikva (IL); Shmuel Suhami, Petah Tikva (IL)

( * ) Notice: Subject to any disclaimer, the term of this patent is extended or adjusted under 35 U.S.C. 154(b) by 0 days.

(21) Appl. No.: 14/076,237

(22) Filed: Nov. 10, 2013

(51) Int. Cl.
*H04R 25/00* (2006.01)
*A61F 11/04* (2006.01)
*A61N 1/36* (2006.01)
*A61N 2/00* (2006.01)

(52) U.S. Cl.
CPC ............ *A61F 11/04* (2013.01); *A61N 1/36032* (2013.01); *A61N 2/002* (2013.01); *H04R 25/43* (2013.01)

(58) Field of Classification Search
CPC ...... H04R 25/00; H04R 25/55; H04R 25/558; H04R 2225/49; H04R 2460/01; H04R 25/602; H04R 2225/31; H04R 2225/33; H04R 2225/023; H04R 2225/025
USPC ......... 381/312–318, 320–321, 323, 327–328, 381/331
See application file for complete search history.

(56) References Cited

U.S. PATENT DOCUMENTS

| | | | |
|---|---|---|---|
| 6,205,420 B1 | 3/2001 | Takagi et al. | |
| 6,236,970 B1 | 5/2001 | Imai et al. | |
| 7,412,378 B2 | 8/2008 | Lewis et al. | |
| 7,760,898 B2 * | 7/2010 | Howell et al. | 381/327 |
| 8,553,910 B1 * | 10/2013 | Dong et al. | 381/327 |
| 2004/0196998 A1 | 10/2004 | Noble | |
| 2007/0041600 A1 | 2/2007 | Zachman | |
| 2009/0103744 A1 | 4/2009 | Klinghult et al. | |
| 2010/0298626 A1 | 11/2010 | Andersson et al. | |
| 2011/0301404 A1 | 12/2011 | Bern | |
| 2012/0278070 A1 | 11/2012 | Herve et al. | |
| 2013/0007949 A1 | 1/2013 | Kurs et al. | |
| 2013/0033118 A1 | 2/2013 | Karali et al. | |
| 2013/0051585 A1 | 2/2013 | Karkkainen et al. | |
| 2013/0090520 A1 | 4/2013 | Redfield et al. | |
| 2013/0163791 A1 | 6/2013 | Qi et al. | |
| 2013/0202140 A1 | 8/2013 | Asnes | |
| 2013/0208935 A1 | 8/2013 | Hakansson et al. | |
| 2013/0225915 A1 | 8/2013 | Redfield et al. | |

OTHER PUBLICATIONS

Yusuf Tufail, Transcranial Pulsed Ultrasound Stimulates Intact Brain Circuits, DOI 10.1016/Neuron 66, 681-694, Jun. 10, 2010 *2010 Elsevier Inc.
Wen Qin Neural Pathways Conveying Novisual Information to the Visual Cortex. Neural Plasticity; vol. 2013 Article ID 864920, 14 pages—http://dx.doi.org/10.1155/2013/864920.

* cited by examiner

*Primary Examiner* — Suhan Ni

(57) ABSTRACT

The invention describes a hearing improvement device including components for training the brain to connect and stimulate the auditory and visual corteces and strengthen pathways between them, in order to overcome the shortcomings of the damaged auditory channel.

11 Claims, 9 Drawing Sheets

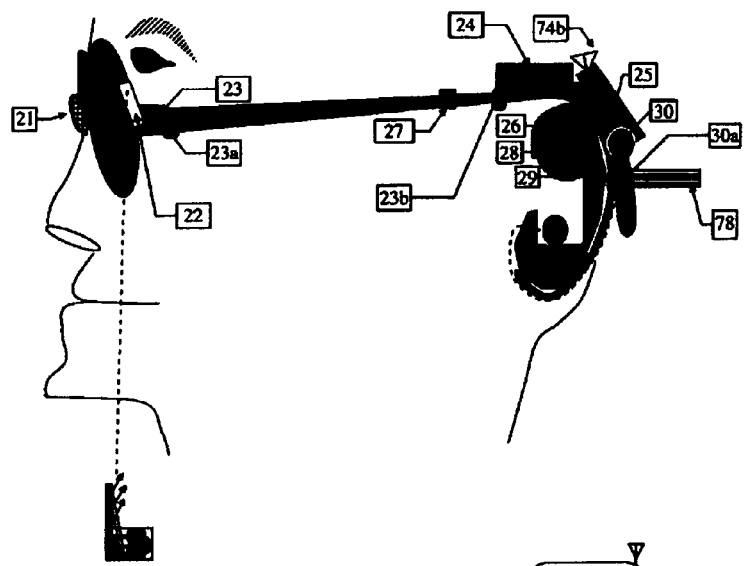
Fig. 2
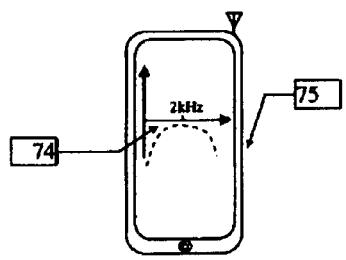
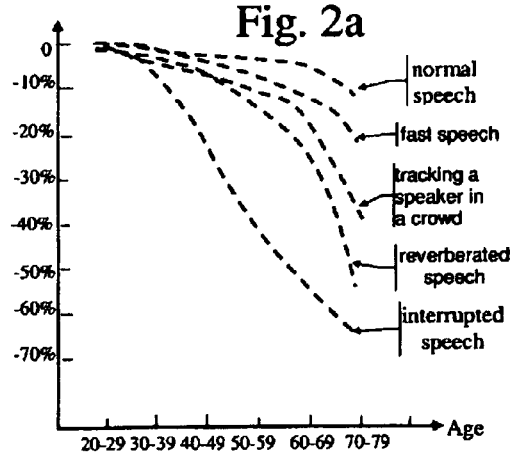
Fig. 2a
Fig. 2b $$\sum_{f_{i}=1...8}^{A} \begin{Bmatrix} I_{f(i)}(F_R[t]) + I_{f(i)}(B_R[t+\Delta t_1]) + \\ I_{f(i)}(F_L[t]) + I_{f(i)}(B_L[t+\Delta t_2]) + \\ I_{f(i)}(F_R[t]) + I_{f(i)}(B_L[t+\Delta t_3]) + \\ I_{f(i)}(F_L[t]) + I_{f(i)}(B_R[t+\Delta t_4]) + \\ I_{f(i)}(F_R[t]) + I_{f(i)}(F_L[t]) \end{Bmatrix}$$

Fig. 6
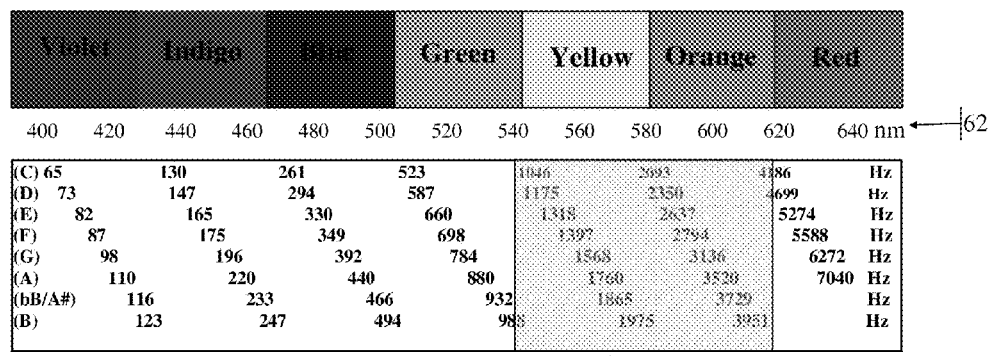
| Octave | frequency (Hz) | substitute frequencies (Hz) |
|---|---|---|
| C | 65 | 130-261-523-1046 |
| E | 82 | 165-330-660-1318 |
| G | 98 | 196-392-784-1568 |
| bB/A# | 116 | 233-466-932-1835 |
| C | 130 | 261-523-1046 |
| E | 165 | 330-660-1318 |
| G | 196 | 392-784-1568 |
| bB/A# | 233 | 466-932-1835 |
| C | 261 | 523-1046 |
| E | 330 | 660-1318 |
| G | 392 | 784-1568 |
| bB/A# | 466 | 932-1835 |
| C | 523 | 1046 |
| E | 660 | 1318 |
| G | 764 | 1568 |
| bB/A# | 932 | 1835 |
| Octave | frequency (Hz) | substitute frequencies (Hz) |
|---|---|---|
| C | 4186 | ---------- |
| E | 4699 | (2)x(2350) |
| G | 5274 | (2)x(2637) |
| bB/A# | 5588 | (2)x(2794) |
| C | 6272 | (2)x(3136) |
| E | 7040 | (2)x(3520) |
| G | 7459 | (2)x(3729) |
| bB/A# | 7902 | (2)x(3951) |
| C | 8382 | (3)x(2794) |
| E | 10548 | (3)x(3516) |
| G | 12544 | (4)x(3136) |
| bB/A# | 14916 | (4)x(3729) |
| C | 16744 | (4)x(4186) |
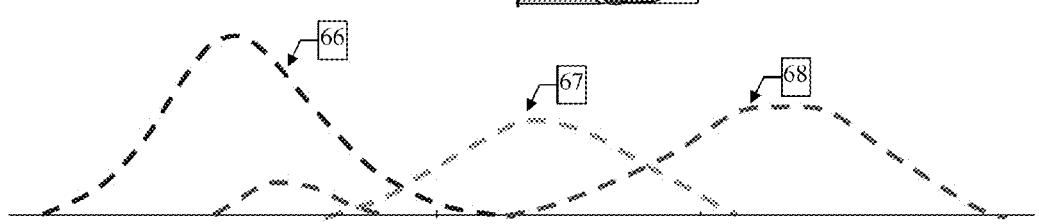

HEARING DEVICES BASED ON THE PLASTICITY OF THE BRAIN

FIELD OF THE INVENTION

This invention relates to hearing devices

REFERENCE TO RELATED APPLICATIONS

This application claims the benefit of U.S. patent application Ser. No. 13/495,648 titled "Audio Communication networks" filed on 13 Jun. 2012, and U.S. patent application Ser. No. 13/682,352 titled "Social network with enhanced audio communications for the Hearing impaired" filed on 20 Nov. 2012 incorporated herein in their entirety by reference.

BACKGROUND

Current hearing aid technology deals with correcting the detrimental effects caused by the damaged inner and middle ear and the cochlea in particular. The main tool used in the various inventions is the non-linear amplification of the impaired sound frequencies.

However it is by now clear that the benefits of the multi-channel non-linear amplifications are limited in attaining the goal of speech "understanding".

Lately, in many healthcare fields, it has been shown that taking advantage of the plasticity of the brain, many physical impairments may be alleviated, if not resolved.

The goal of this invention is to enable "to hear" the unheard or badly heard sound frequencies, by training the brain to connect the auditory channel with the visual channel and use stimulations of the eye in order to help the brain decipher language when the auditory channel by itself is at a loss, due to missing frequencies.

Various effects illustrate the auditory processing of the brain in order to optimize understanding of speech. For example the phenomenon known as the "missing fundamental" consists in the brain determining the fundamental sound frequency after hearing harmonic frequencies of the said fundamental frequency, and substituting the "missing fundamental" in trying to decode a word.

It has also been observed that the brain cannot distinguish between subsequent sounds "heard" within 3-4 msecs and just interprets the sum of the two as the signal heard.

The joint processing of information between the auditory cortex and the visual cortex is illustrated by what is known as the "McGurk illusion", where a phoneme heard concurrently with a video of the mouth enunciating a different phoneme, is interpreted by the brain as the phoneme heard in the video. This illusion shows that there are pathways between the visual cortex and the auditory cortex where the two try to arrive at a common conclusion; in this case the phoneme heard accompanied by a picture of the mouth articulating it, trumps the phoneme that reached only the auditory cortex.

McGurk and MacDonald [Nature 264, 746-748], also showed that when the auditory and visual signals may, each, point to several possibilities, the brain will select the option commonly favored by both. For example the phonemes "ba" and "da" can be confused by the auditory cortex while the phonemes "ga" and "da" can be confused by the visual cortex. Thus when the phoneme "ba" is articulated and at the same time a video of the lips saying "ga" is shown, the brain will conclude that "da" was said, neither "ga" nor "ba".

Meredith et al. report in the Proceedings of the national Academy of Sciences IPNAS 70 2011 108 (21) 8856-8861 "crossmodal reorganization in the early deaf, switches sensory but not behavioral roles of auditory cortex", that:

"Recordings in the auditory field of the anterior ectosylvian sulcus of early-deafened adult cats, revealed robust responses to visual stimulation as well as receptive fields that collectively represented the contralateral visual field. They conclude that "These results demonstrate that crossmodal plasticity can substitute one sensory modality for another while maintaining the functional repertoire of the reorganized region".

Laura Ann Petitto et al in Proceedings of the National Academy of Sciences PNAS 2000 97 (25) 13961-13966; "Speech-like cerebral activity in profoundly deaf people processing signed languages: Implications for the neural basis of human language" note that:

"For more than a century we have understood that our brain's left hemisphere is the primary site for processing language, yet why this is so has remained more elusive. Using positron emission tomography, we report cerebral blood flow activity in profoundly deaf signers processing specific aspects of sign language in key brain sites widely assumed to be unimodal speech or sound processing areas: the left inferior frontal cortex when signers produced meaningful signs, and the planum temporale bilaterally when they viewed signs or meaningless parts of signs (sign-phonetic and syllabic units). Contrary to prevailing wisdom, the planum temporale may not be exclusively dedicated to processing speech sounds, but may be specialized for processing more abstract properties essential to language that can engage multiple modalities. We hypothesize that the neural tissue involved in language processing may not be prespecified exclusively by sensory modality (such as sound) but may entail polymodal neural tissue that has evolved unique sensitivity to aspects of the patterning of natural language. Such neural specialization for aspects of language patterning appears to be neurally unmodifiable in so far as languages with radically different sensory modalities such as speech and sign are processed at similar brain sites, while, at the same time, the neural pathways for expressing and perceiving natural language appear to be neurally highly modifiable.

Renaud Boistel et al. in Proceeding of the National Academy of Sciences 10.1073 PNAS 1302218110 Sep. 3, 2013 note that: "Gardiner's Seychelle fog, one of the smallest terrestrial terapods, resolves an apparent paradox as these seemingly deaf fogs communicate effectively without a middle ear. Acoustic playback experiments conducted using conspecific calls in the natural habitat of the fogs provoked vocalizations of several males, suggesting that these frogs are indeed capable of hearing. This species thus uses extra-tympanic pathways for sound propagation to the inner ear. Our models show how bone conduction is enhanced by the resonating role of the mouth and may help these frogs hear".

There is now extensive anatomical and physiological evidence from a range of species, that multisensory convergence occurs at the earliest levels of auditory cortical processing. Phased array ultrasound beams may be focused on a relatively small spot, thus delivering concentrated energy onto the desired locality in the brain. There is extensive evidence that irradiating damaged body organs, such as bone-fractures or missing teeth, with low intensity ultrasound, causes re-growth of the damaged parts. Y. Tufail et al in "Transcranial Pulsed Ultrasound Stimulates Intact Brain Circuits" report that "we found that ultrasound triggers TTX-sensitive neuronal activity in the absence of a rise in brain temperature (<0.01 C)" Low intensity pulsed ultrasound is known to help healing lacerated muscles and various soft tissues. Although the exact mechanism of healing is not known, it is probably linked to the amount of energy deposited in the cells that energizes certain processes. We therefore conjecture that sound energy of the right frequency and intensity deposited in the brain will enhance neuron activity in that spot. Specifically, energizing neurons in the auditory and visual corteces simultaneously may promote and strengthen existing coordinating processes.

There are testimonies of people that say that they "hear voices". These testimonies indicate that the brain is able to generate internal sounds similar to the sounds originating through the auditory channel.

Our goal is to cause quasi-deaf people to "hear voices" generated mostly in the brain, by stimulating the brain "to put together" partial information received through the auditory channel with correlated information delivered through the visual channel and "GUESS" what was said.

SUMMARY OF THE INVENTION

The present invention, is a device that enables to train the brain of a hearing impaired person to correlate unheard or badly heard sound frequencies with "substitute frequencies", visual color sequences and pictures of the mouth enunciating said phonemes concurrently, while triggering the corresponding areas of the auditory and visual corteces simultaneously, with focused ultrasound beams and magnetic stimulations.

Once trained and the one-to-one correspondence between sound frequencies, "substitute frequencies" and color wavelengths are well established in the brain, we conjecture that a relatively simple pair of Eyeglasses incorporating a processor for translating the initial sound frequencies to "substitute frequencies", bone conduction transducers to transmit the substitute vibrations indirectly to the cochlea and a color light source illuminating the eye from the side, will greatly improve the hearing capabilities of the hearing impaired persons. We also conjecture that stimulating the auditory and the visual corteces simultaneously with sounds of the same frequency will strengthen the one-to-one connection between sounds and colors. The auditory and visual corteces may also be stimulated simultaneously with magnetic energy delivered by resonant coils that enable to traverse the brain with little loss of energy. This little amount of energy may be increased at will by detuning the resonance between the coils. A multiplicity of resonant coils placed at strategic positions around the head may cumulatively deposit energy at selected regions of the brain, for example on the auditory cortex. We conjecture that depositing extra energy at the right moment will "cause" the brain to work harder and "decipher" speech with the substitute frequencies.

The unheard or badly heard frequencies may be determined by taking audiograms of the ears and the "substitute frequencies" established during the training period. The substitute sound frequencies may be generated by a bone conduction (BC) speaker of a specific design shown in this application. The (BC) speakers transfer the vibrations to the skull, bypassing the outer ear" and the "middle ear" that may be damaged and reach the cochlea in the inner ear. As the bandwidth of the (BC) speaker is lesser than that of the (AC) speaker, in cases where the causes of the hearing impairment may not be clear, it is advantageous to use the (AC) speaker tugged to the ear canal in addition to the (BC) transducer pressed onto the skull.

Simultaneously with exciting the cochlea by a given sound frequency, the hearing impaired person's eye is visually excited by a colored light of corresponding wavelength, such that a one-to-one correspondence is gradually established between the sound frequencies and the light wavelengths.

The light excitation may be generated either by a miniature tricolored light source where the power of each LED is controlled, or by a colored display in front of the person's eyes.

Simultaneously with the cochlea and eye excitation, the corresponding auditory and visual cortex areas that process the transduced electrical signals, are also excited by twin external transcranial phased-array ultrasound beams that converge on the desired area. The ultrasound emitters are held in place against the crane by one or more ratcheted bands around the crane.

The frequencies of each of the pair of phased-array ultrasound beams converging on the corresponding auditory and visual corteces excited areas, are slightly different, so that at the focal region their interference generates a difference signal of the same frequency as the frequency of the original sound signal. We conjecture that the brain will establish a triple correspondence between the signals coming from the eye, the cochlea and the transcranial signals and will interpret the sum as the desired sound, even when the signal from the cochlea may be weak and for some frequencies nonexistent.

An additional strategy for reinforcing the brain's interpretation of the "correct" frequency in the context of a word, is to train it to correlate the unheard frequency with a substitute frequency that is "better" heard by the cochlea. The substitute frequencies of badly heard or unheard frequencies may be the higher frequency harmonics and sums of frequencies generated within a time window of less than 3 msec that the brain will interpret as one higher frequency. Thus a translation "look-up-table" may be generated that translates the original speech frequencies detected by microphones to their "harmonics" or "time-squeezed" frequencies before delivering them to the bone conduction speaker or an audio speaker.

The frequency training of the brain may be enhanced by phoneme training that consists in pronouncing phonemes while simultaneously displaying the sequence of colors that are related to the sound frequencies. The training may be further enhanced by displaying the lips of a person pronouncing the phoneme.

The components of the training system may be incorporated onto eyeglasses and a cap with a long visor worn by the trainee, where the system is controlled and managed by a smartphone. The extremely thin, flexible display monitor, connected by bluetooth to the smartphone, lies at the front of the visor and may easily be flipped onto a position in front of the eyeglasses.enabling the eyeglasses wearer to view colored images transmitted by the cellphone, for example in the "face time" mode of the iPhone. The eyeglasses bows incorporate microphones at the front and back ends enabling to assess the direction of incoming sound and thus reject surrounding noise, thus greatly improving speech understanding. A bone conducting transducer of our design, able to tailor sound sequences out of single frequencies are incorporated at the back of the bows behind the ear, next to the mastoid bone. The bone conducting vibration transducer is able to generate single frequency vibrations and thus enables to measure the "bone conduction audiogram" by the hearing impaired person.

Various colored signals may be generated by a colored light illuminator consisting of miniature (Blue, Green and Red) LEDs controlled by a microprocessor that sets their relative intensities that determine the combined color after mixing, and the absolute intensities that determine the intensity of the end colored light. The illuminators may be incorporated in the front ends of the eyeglasses temples, in which case suitable mirrors direct the output light onto the eyes from the side; if both ears have the same hearing losses, the illuminator may be placed in the middle of the glasses frame and the colored light naturally observed by both eyes. A display viewable through the eyeglasses, also enables to correlate sounds with related images and thus improve hearing. Lip reading of a talking person viewed on the display of the cellphone in a "Face Time" mode, may be transmitted by wireless in real time to the display in front of the eyeglasses.

Relatively large displays may be very thin and suspended from the front rim of the visor of a cap worn by the eyeglasses wearer. The display, the communication hardware and the antenna may be embedded in the rims of the cap as is the battery supplying the power.

Many aspects of "Hearing" improvement depend on eliminating surrounding noise and the way interlocuters talk. We maintain that in addition to finding remedies to the bodily hearing impairments it is as important to reduce all components of "noise" and make the necessary adaptations to the way others talk.

In our system we try to substantially eliminate noise using 3 strategies. One strategy is by letting the hearing impaired person, to limit his "listening cone" to cover only the space covered by his interlocutor. This goal is implemented using 4 directional microphones on the forth and back of the temples of the eyeglasses and setting stringent limits to the time delays of the correlated sound reaching them.

The second strategy we use for reducing noise, is to follow speech components in time with a time resolution of 1-2 milliseconds and try to locate the natural "pauses" between phonemes, syllables and words. As noise is, with high degree of probability, present both during "pauses" and during speech segments, subtracting the noise frequencies amplitudes from the following speech frequencies, using a simple algorithm, improves the SNR during speech. This strategy is applicable both to the sound detected by the microphones situated on the eyeglasses temples as it is applicable to the microphone(s) of the smartphone and the bone conduction transducer operated as a microphone.

The third strategy is to use the different frequency response of the air conduction (AC) microphones and bone conduction transducer used as a microphone, and accelerometers that detect vibrations of the crane; cross correlations between the different sensors, differentiate between correlated speech and uncorrelated or weakly correlated surrounding sound noise. The (BC) microphones also strongly detect the eyeglasses hearer's own voice as the mouth cavity resonances generate strong vibrations of the crane.

In this context it is important to note that Bone Conduction transducers may be used both as detectors of vibrations (microphone) and generator of vibrations (speaker).

Bone conduction transducers made with piezoelectric materials have non-linear responses both in intensity and frequency bandwidth. When transmitting vibrations to the crane, it is almost impossible to tailor the frequency response that reaches the cochlea, to compensate for the loss of frequency sensitivities a damaged cochlea has. Consequently this invention comprises a new transducer design, that enables to generate vibrations for each frequency independently of the others and comprises an equalizer that allows to tailor the frequency response. Thus it is possible to take in account the frequency response of the cochlea and the crane bone in order to generate a flat or the desired frequency response that the neurons transmit to the auditory cortex.

The next important feature that improves speech understanding is a knowledge of the speaker's "voice signature", his intonation characteristics, such as the relative intensities and spectra of vowels and consonants in phoneme pronunciation and speed of talking. Such "Voice signature" characteristics of "frequent callers" may be analyzed in advance using a spectrum analyzer application stored in the smartphone, enabling to generate a list of characteristic pronunciations of phonemes. As the Hearer's spectral characteristics and time response are usually different, a one-to-one or a many-to-one look-up table of phonemes may be established, enabling to adapt the incoming phonemes detected by microphones to the hearing characteristics of the recipient and relay the adapted phonemes to the recipient's speaker and ear.

BRIEF DESCRIPTION OF THE DRAWINGS

FIG. 2 illustrates a smartphone controlled Eyeglasses carrying on its bows the components needed to reject audio noise, generate substitute frequencies relayed to the bone conduction (BC) speaker/microphone and color LEDs for illuminating the eye simultaneously with audio frequencies heard.

FIG. 2a illustrates the deterioration of hearing with advanced age for different modes of speech.

FIG. 2b illustrates the subtraction of noise measured during speech pauses from the following syllables and words.

FIG. 6 illustrates the one-to-one correspondence between audio frequencies and color wavelengths for exciting the auditory and visual corteces simultaneously.

DETAILED DESCRIPTION OF THE PREFERRED EMBODIMENTS

The following detailed description, provide a thorough understanding of the invention while omitting specific details, that are known by those skilled in the art.

Figure 1:
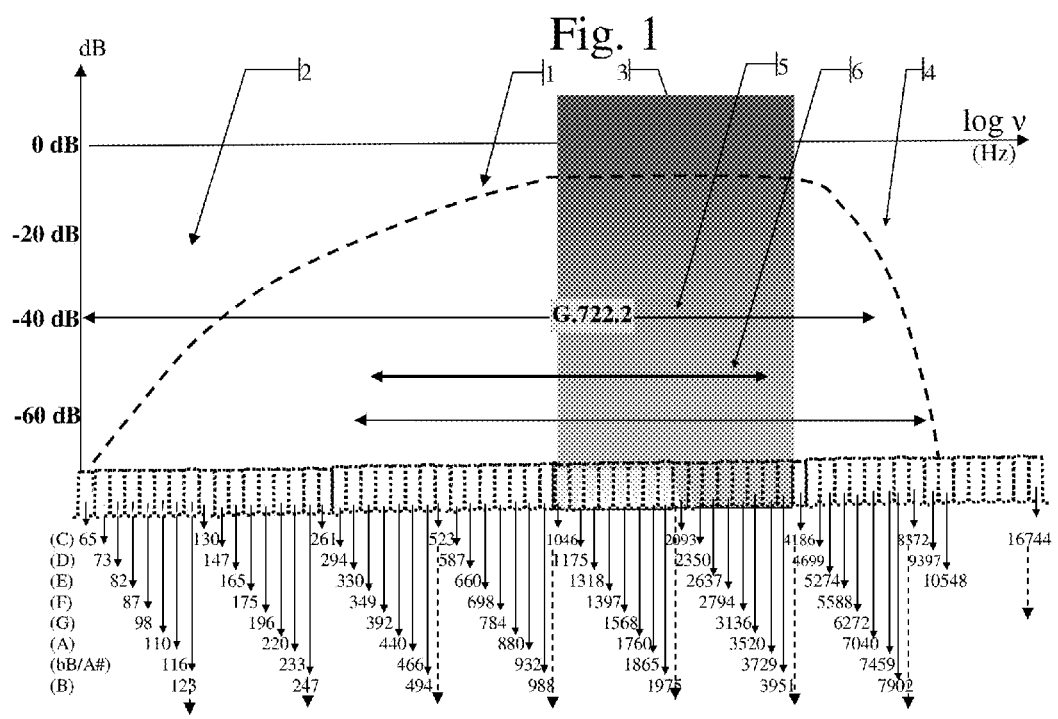
FIG. 1 illustrates a "Hearing threshold" of a person with moderate hearing loss between 65 Hz to 16,744 Hz and substitute frequencies for frequencies below 1 kHz and frequencies above 4 kHz.

Hearing impaired persons exhibit an "audiogram" with diminished response at low and high frequencies. FIG. 1 illustrates a "Hearing threshold" 1 of a person with moderate hearing loss between 65 Hz to 16,744 Hz divided into low frequency 2, mid frequency 3 and high frequency 4 hearing regions. Such an audiogram may be self generated by using the smartphone to generate a series of audio frequencies at varying loudnesses while the person indicates the loudness level at which he ceases to hear the signals. This audiogram shows that the person has "normal hearing" between 1 kHz and 4 khz, but has a moderate-to-steep loss of hearing below 1 kHz and above 4 kHz. In cases of precipitous hearing loss, even the understanding of normal speech in the middle frequencies may seriously be impaired and a Hearing Aid is needed. In cases of severe hearing loss cases, the hearing impaired may only hear even a lower bandwidth of middle frequencies. The new ITU-T G.722.2 standard of Adaptive Multi-Rate Wideband of speech 5 requires a bandwidth of 50 Hz to 7 kHz which is beyond the hearing abilities of most middle-aged people except audiophiles. It is interesting to note that the bandwidth 6 of the Plain Old Telephone Service (POTS) is only 300 Hz to 3400 Hz and people "understand" telephone conversations well "when there is no "noise" on the line; in our opinion that shows that "noise" elimination is extremely important ands because their brains were "trained" to fill in the unheard frequencies.

FIG. 2 illustrates the pair of eyeglasses with electronic components, sensors and transducers that together improve the hearing of the hearing impaired person. In a preferred embodiment the Hearing Eyeglasses components embedded in each of the eyeglasses temples include, a bluetooth RF transceiver with a microcontroller and a large flash memory 74$b$, an infrared LED 21 of sensitivity at 850 nm, a colored light illuminator 22 consisting of 3 LEDs (blue-green-red) controlled by the microcontroller, 2 unidirectional microphones 23$a$ and 23$b$, a rechargeable $LiPO_4$ battery 24, a Bone Conduction (BC) speaker/microphone 25, a quad comparator/gate 26, an accelerometer 27, a DSP 28, a CODEC 29 comprising a wide band equalizer and delay generators, an (AC) speaker/microphone 30 hidden behind the ear that can be released and inserted into the ear canal. The microcontrollers situated in the temples may communicate between them by coaxial wires embedded in the temples of the eyeglasses and the rims of the glasses. The tips of the temples are tightly interconnected by a ratcheted band 78 behind the head, thus pressing the bone conduction speaker/microphones against the skull. The microcontrollers control the traffic on the temples of the eyeglasses, and the DSPs process the algorithms that reduce noise, and determine the proper amplification of different frequency bands.

The various instructions to the components of the system may be conveyed by coded "taps" on the accelerometers or the microphones. They enable, for example to change the volume of the respective speakers. Taps may be interpreted as "0" or "1" depending on the frequency of the correlating 1 tap with "0" and 2 short sequential taps as "1". Different sequences may be used for selecting programs, devices and their features such as increasing or decreasing the volume of a speaker or a frequency of the (BC) transducer. A prerecorded menu of the 1 "Tap" features may be delivered to the ear for example after 3 sequential taps.

Unidirectional microphones 23$a$ and 23$b$ detect sounds coming mainly from the front. The time delays between the 4 microphones on the 2 temples determine the direction of the sound and serve to eliminate all sounds that do not abide by the timing constraints. The microcontrollers embedded in the two temples communicate by the coaxial cables embedded in the temples and the rims of the eyeglasses frame.

Zinc-air high capacity, model 675 button cell batteries serve as back-up to the rechargeable $LiPO_4$ batteries.

The frame of the eyeglasses may also hold a miniature wideband video camera 21 able to image objects in obscure locations. The video camera may be used to take a sequence of pictures of the mouth of the person with whom the eyeglasses wearer is having a conversation with, while recording the short conversation. The frame-by-frame display played concurrently with the related prerecorded phoneme, serve to train the brain. The camera may have a wide band sensitivity in order to detect infrared light and thus image people talking in the dark or in obscure places.

FIG. 2$a$ shows the deterioration of hearing with advanced age for different modes of speech. While listening to normally articulated speech, a persons understanding of normal speech, declines by some 10 percent by the age of 70 to 79; listening to fast talking people makes understanding twice as difficult; speech understanding then declines by 20% by the age of 70 to 79. It also illustrates the steep decline of speech understanding with age when the interlocutor is in a crowd, when there is echo in the room or when his interlocutor talks with interruptions.

FIG. 2$b$ illustrates the process of noise elimination from speech. Speech is built out of phonemes, syllables and words interspersed by pauses in between. The average english word duration is around 250 msecs while "pauses" between syllables are around 50 to 100 msec.

Consequently noise intensity and spectra can be measured during such "Pauses" 31 and subtracted from following speech 31$a$ segments. The beginning of a pause may be detected by a steep drop in intensity and the end of the pause by a steep increase of intensity. These inflection points may be determined by following the sample amplitudes when sampling the speech, for example at 44 kHz. The beginning of a pause may be determined by finding the 10 samples whose average intensities are lower from the previous ones and approximately the same from the following 10 ones. The end of a pause then is the 10 samples whose average intensity is approximately the same as the previous ones and the following samples average intensity starts growing on the average. The "pause" time may then be defined as the middle 90% between the inflection points. Sound intensity rate during the pause period in the frequency domain may then be subtracted from the following speech segments also in the frequency domain.

As surrounding noise doesn't change fast, the process of measuring noise at "pauses" is repeated only from time to time and the last measured noise intensity and spectra are subtracted from ongoing speech signals for as long that the volume of sound doesn't change much.

FIG. 3$a$ illustrates the processing of speech arriving from the front, from the interlocutor or from the TV. It illustrates the principles for determining the direction of sound by measuring the time delays of sound between the 4 unidirectional microphones, $F_R$, $F_L$, $B_R$, and $B_L$ situated on the temples of the eyeglasses. The time delays of the sound waves arriving at the 4 microphones, $\Delta t_1$, $\Delta t_2$, $\Delta t_3$, $\Delta t_4$, and $\Delta t_5$ being known in advance, the way to select the sounds arriving from the front direction out of all the sounds reaching the microphones is as follows:

decompose the signals in each sample in the frequency domain using, (i) digital filters, and after adding the proper delays, sum the five streams of signals in the frequency domain, then add All (i=n) frequency streams and Pass through a differential amplifier to select the cumulative speech signals above random sound signals baseline.

Adding the signal streams for each frequency, with proper delays 31 stemming from their mutual distances in space, causes the amplitude of speech signals coming from the front to overlap and reinforce each other, while sound signals coming from other directions are distributed at random on a time scale.

Adding all the frequency signals further reinforces the speech signals in comparison with random noise or sound with a different frequency content.

Finally, passing the cumulative signal through a differential amplifier enables to reject all the non-directional sounds and preserve the directional speech signal. This directional signal may then be processed by properly amplifying the frequency bands that are not well sensed by the hearing impaired. The processed signal may be delivered to the ear canal of the hearing impaired person through an air conduction (AC) speaker 30a and/or through a bone conduction (BC) transducer 25 to his crane that transmits the vibrations to the cochlea. In case of using only the bone conduction speaker to deliver the audio signal through crane vibrations, it is important to plug the ear canal with a sound reflecting cap, in order to minimize the surrounding sound that reaches the hearing impaired person's ear canal.

Figure 3A:
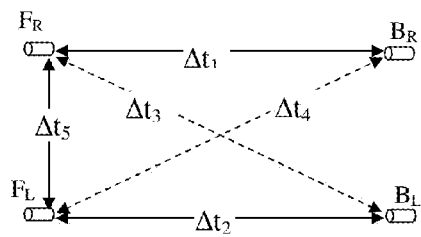
FIG. 3a illustrates the subtraction of surround sound that does not reach the eyeglasses wearer directly from the front.
Figure 3B:
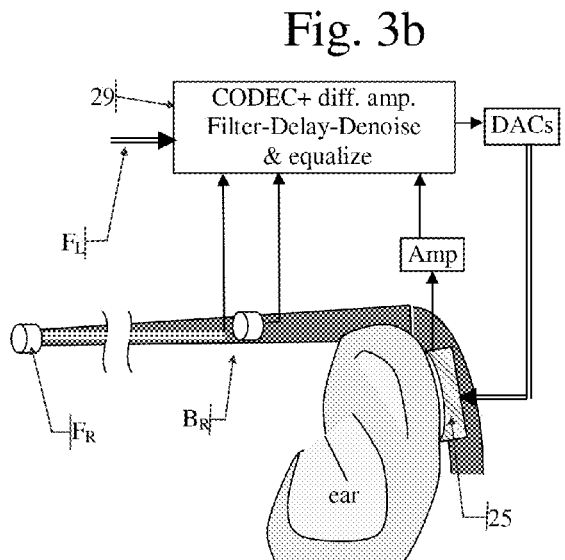
FIG. 3b illustrates the process of noise elimination before transmitting the speech signals to the (BC) transducer and the dual functionality of the (BC) transducer both as a microphone and a speaker.
Figure 5:
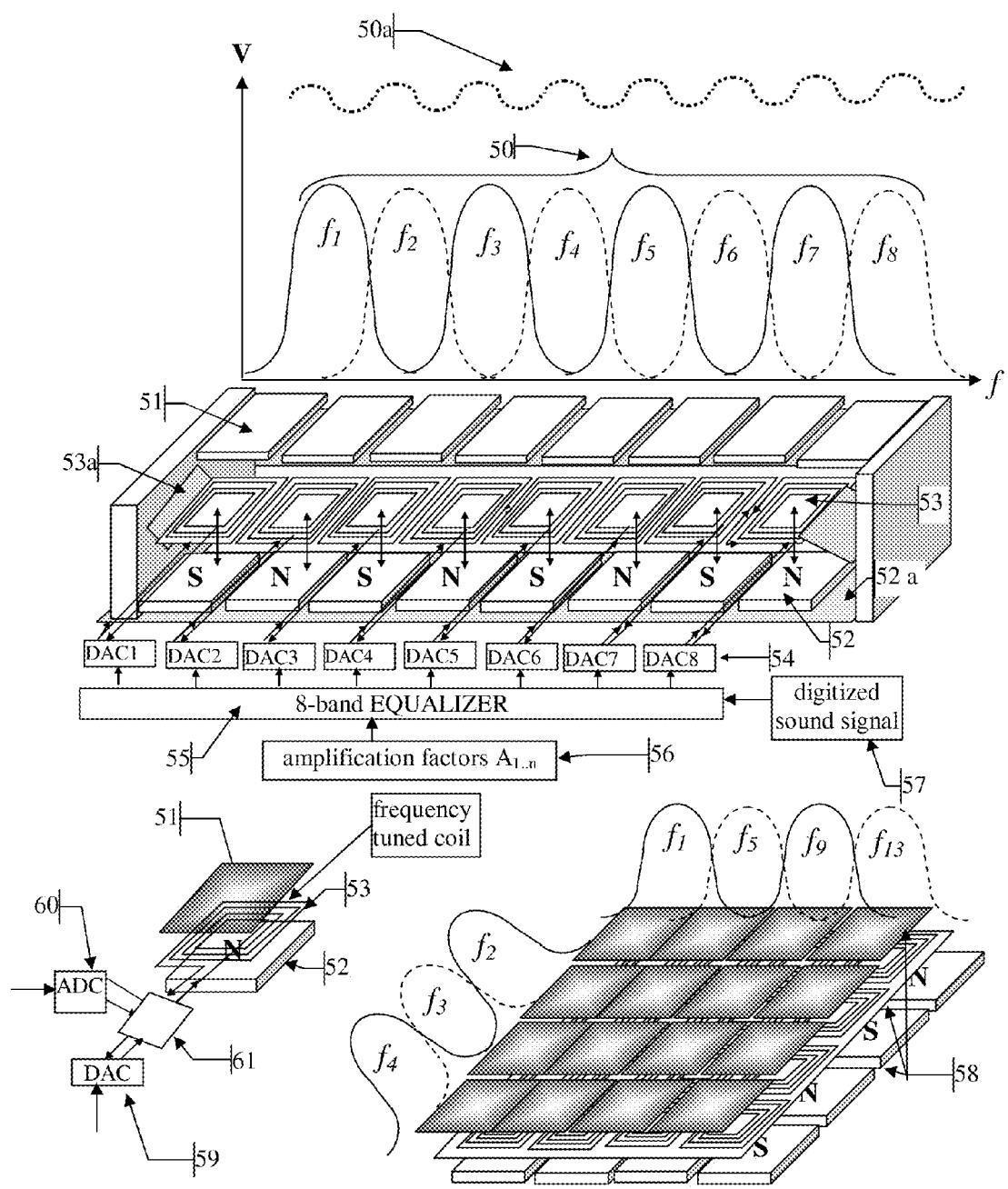
FIG. 5 illustrates a mechanical vibration producing transducer with separate controls over each band of frequencies, suitable to transmit audio vibrations by bone conduction and serve also as a sensor of vibrations of the skull.

FIG. 3b illustrates a simplified diagram of the process of noise elimination before transmitting the speech signals to the (BC) transducer illustrated in FIG. 5 and the dual functionality of the (BC) transducer both as a microphone and a speaker. As illustrated in FIG. 3a above, the outputs of the three microphones $F_R$, $F_L$ and $B_R$ are properly delayed in the CODEC 29 and filtered by bi-quad filters. The (BC) transducer 25 operates half of the time (for example for 1 millisecond) as a microphone and the second half as a speaker. The outputs of the (BC) "microphone" which are already in the frequency domain are properly amplified (or attenuated) to equalize their average level to that of the (AC) microphones. As the amplified outputs of the (BC) "microphone" are "lagging" in time in comparison to the speech components of the (AC) microphones, their signals are further delayed according to their distances from the (BC) microphone.

Figure 3C:
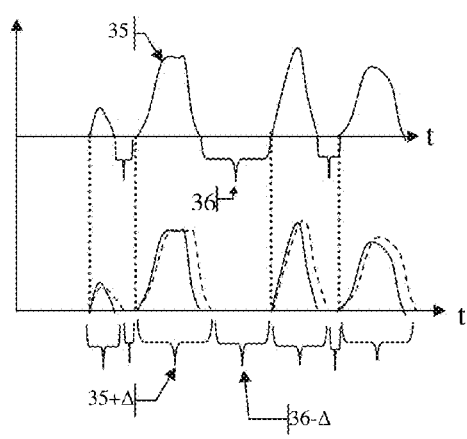
FIG. 3c illustrates the correction of fast speech by enlarging the periods of speech while reducing the intervals between phonemes and syllables.

The properly delayed streams of the 3 microphones and the (BC) microphone are added and passed through differential amplifiers that subtract the uncorrelated frequencies and transmits the correlated ones through DACs 54 to the coils 53 of the (BC) transducer, thus causing the plates 51 glued to the coils to vibrate at the frequency of the current passing through the coil. 435 FIG. 3c illustrates a way to improve understanding of fast talk by expanding the time it takes to pronounce a phoneme or syllable on account of the silence intervals between phonemes, syllables or words. This is done by enlarging the periods of speech 33 to 33+Δ while reducing the intervals between phonemes and syllables also by the same amount 34 to 34-Δ. This may be accomplished by expanding the samples duration above a given level (noise) by a given amount and reducing the duration of the following samples by the same amount, by changing the sampling clock.

Figure 4:
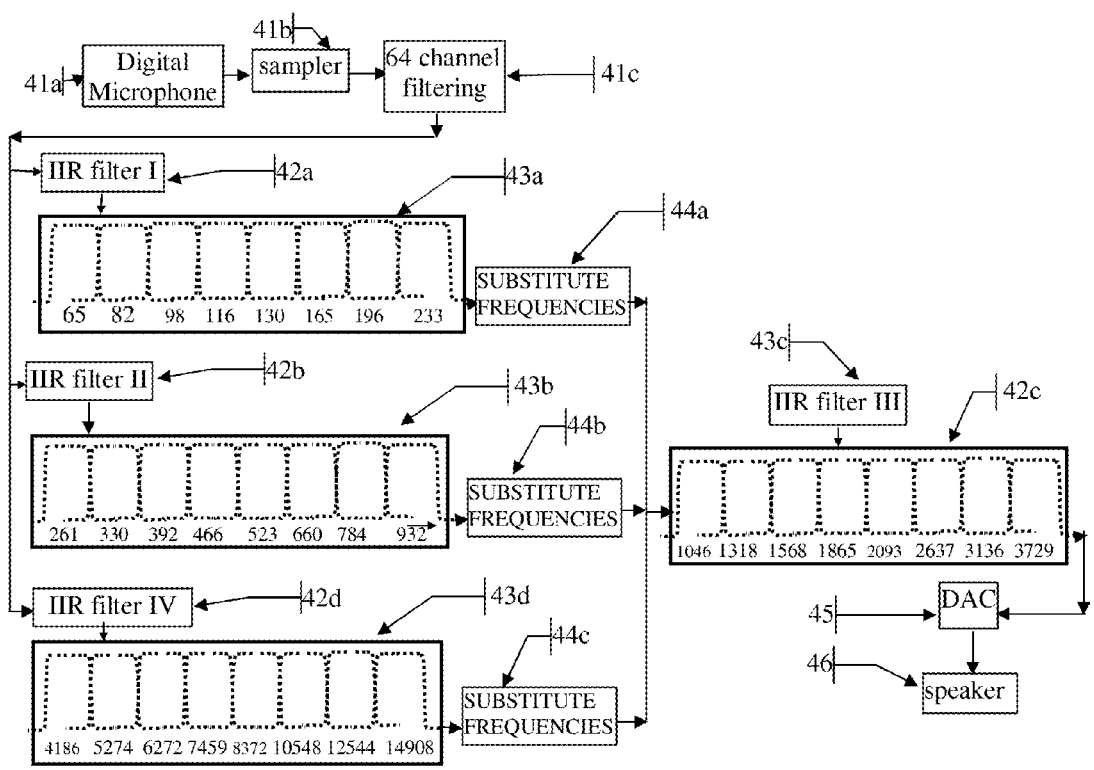
FIG. 4 illustrates the substitution of unheard or badly heard audio low and high frequencies with frequencies in the 1 to 4 kHz range.

FIG. 4 illustrates the sampling of the voice signal detected by a digital microphone, its decomposition in the frequency domain by filtering it with an IIR filter, substitution of unheard or badly heard low and high frequencies with frequencies in the 1 to 4 kHz range, adding the amplitudes in the frequency domain and applying the resultant amplitudes onto the (BC) transducer.

FIG. 5 illustrates a mechanical vibration producing transducer with separate controls over each band of frequencies, suitable to transmit audio vibrations by bone conduction and serve also as a sensor of vibrations of the skull.

The vibration producing transducer is composed of a multiplicity of solid elements 51 that each may vibrate at a different frequency 50.

The elements 51 are solid, non-conductive and non-magnetic and may be of plastic or light ceramic. Electrical miniature flat, spiral shaped coils 53 that carry alternating currents supplied by digital-to-analog-converters (DAC) 54, are glued to the back of the elements 51; the adjacent coils are wound in opposite directions.

The array of coils are in turn glued to a thin elastomer diaphragm 53a in close proximity above an array of fixed magnets 52 having alternating poles between adjacent magnets. The stationary magnets are glued to a non-magnetic back structure 52a. Adjacent magnets have their north and south poles flipped in opposite directions so that the coils facing them are either attracted or repealed depending on the direction of the current in the coil.

The transducer may generate planar vibrations by having its segmented diaphragm 53a move forth and back, the different segments vibrating at different frequencies. The original electrical signal 57 is first passed through an equalizer 55 that decomposes it into its frequency bands; each of the frequency band signals may be amplified separately 56 by a different amount and fed to the coils 53 independently and phase locked.

In such an architecture the parts of the diaphragm glued to the coils will vibrate at different frequencies and at different amplitudes enabling to better shape the spectra of the vibrations. Such a transducer may generate single frequency vibrations for training the cochlea. The transducer does not have to be flat; the vibrating elements may be slightly curved and the totality of the elements form a curvature to better adjust to the local curvature of the crane, thus transmitting the vibrations with lesser pressure.

The elements and magnets of the transducer may be miniaturized; for example a 16 frequency array with 3×3 mm elements 58 (frequencies) may be as small as 1.5×1.5 cm and a 64 element array may approximately be 1" square.

The transducer may also be used as a sensitive vibration microphone 60 where the vibrations transmitted to a plate 51 will cause the coil 53 on top of the magnet to vibrate, generating an induced current that can be amplified and digitized 60.

FIG. 6 illustrates the establishment of a one-to-one correspondence between audio frequencies 63 transmitted to the auditory channel and color wavelengths 62 seen by the visual channel. The one-to-one correspondence is also established between the volume of the audio frequencies and the intensity or brilliance of the colors. As mentioned above the ability of the brain to substitute harmonic frequencies in lieu of a missing fundamental frequency in trying to decipher a "word" when the missing fundamental is missing, has been observed. Consequently the low frequencies from 65 Hz to 932 Hz can be replaced by their harmonic substitutes from 1046 Hz to 1835 Hz as illustrated in table 64. The "cycle" of audible tones is based on the harmonic relations modulo the octave. We can just associate each tone with its "equivalent" in other octaves.

As to the frequencies above 4 kHz that in the illustrated example, the hearing impaired does not hear well, we make the following observation that although the cochlea response to avibrations is of the order of several hundred microseconds, the neurons response latency is much larger, in the order of one to several milliseconds. When several inputs arrive within this 495 latency period the result is a summation. We therefore conjectured that high frequencies that are unheard or badly heard may be replaced by 2,3 or 4 times middle frequencies as shown in table 65, with approximately 1 msec intervals; the middle frequencies although well coded by the cochlea and delivered sequentially to the nervous system, will be integrated into one higher frequency and the brain will get the sum of the sequence and interpret them as one 500 vibration of a higher frequency. Thus for example an "s" that is pronounced at approximately 5200 Hz may be transmitted by a (BC) transducer to the cochlea as two sets of vibrations of 2600 Hz each at 1 msecond interval between the sets; the cochlea will transduce them to 2 signals of 2600 Hz each, however the slow to react synapses will sum them and transmit to the auditory cortex a 5200 Hz signal.

To "convey" to the auditory cortex what "we mean" when the low or high frequencies are substituted by middle frequencies that are better coded by the cochlea, we can take advantage of the pathways between the auditory and visual corteces and train the brain to establish a one-to one correspondence between optical wavelengths (colors) and sounds.

To help the brain decipher a word in the language context, every time a "substitution vibration" is delivered to the cochlea, we also project to the eye the wavelength (color) corresponding to the original frequency (vibration). For example when the word "mother" is articulated the "m" is usually articulated as a 270 Hz sound wave by the mouth. This sound may not be well deciphered by the cochlea and we may prefer to substitute the harmonic frequency that is 4 times the original frequency, 1080 Hz. However the 1080 Hz vibration may also correspond to the consonant "p"; therefore if we deliver visually a bluish signal of 470 nm and the brain was previously trained to correlate the 470 nm light with the 270 Hz vibration, the brain would know that the 1080 vibration is an harmonic of the fundamental frequency of 270 Hz.

The training of the brain to recognize substitute frequencies for replacement of unheard or badly heard frequencies and strengthening this exercise by establishing a one-to-one correspondence with colors, aided by lip reading may be carried repetitively a large number of times and the "learning" rate checked periodically. It is also possible to carry-on the exercises under hypnosis and get the help of the "subconscious" mind to establish to one-to-one correspondences.

The brain however performs an immense number of tasks, consciously and inconciously, and some of them involve colors in various contexts. The task of linking colors to sounds has therefore to be defined in a specific context and not as a general feature to be performed at all times. We wouldn't want that every time a Red color is perceived, to hear an 8 kHz whistle. Therefore the task of correlating colors with sound frequencies has to be limited to certain tasks, only in the context of "language" for example or when the task is preceded by a "code" and terminated by a different code. That is like tasks instructed to do during hypnosis, not before or after. The brain can be trained to respond to several color codes; using BLUE for "0" and RED for "1" for example and a multitude of color codes of several bits could be devised to direct the brain to perform certain tasks. It is also possible to train the Brain to generate the sound frequency corresponding to a given wavelength only in the presence of a third signal, for example a tactile signal. For example "rubbing your right ear" may start and "rubbing your left ear" may end the session of correlating colors and sound frequencies.

Another impetus to start correlating colors with sound frequencies may be, by irradiating both the visual and auditory corteces with low intensity ultrasound beams and energizing them to start cooperate.

The visual color signal may be generated by 3 low power LEDs (Blue 66, Green 67, Red 68) in a proportion determined by the microcontroller on the temple of the eyeglasses. The colored light source 22 is positioned at the front end of the eyeglasses temple; the light is reflected by 2 mirrors onto the direction of the eyeglasses bearer's eye.

The intensity of the colored light may also reflect the volume of the sound it is correlated with.

Figure 7:
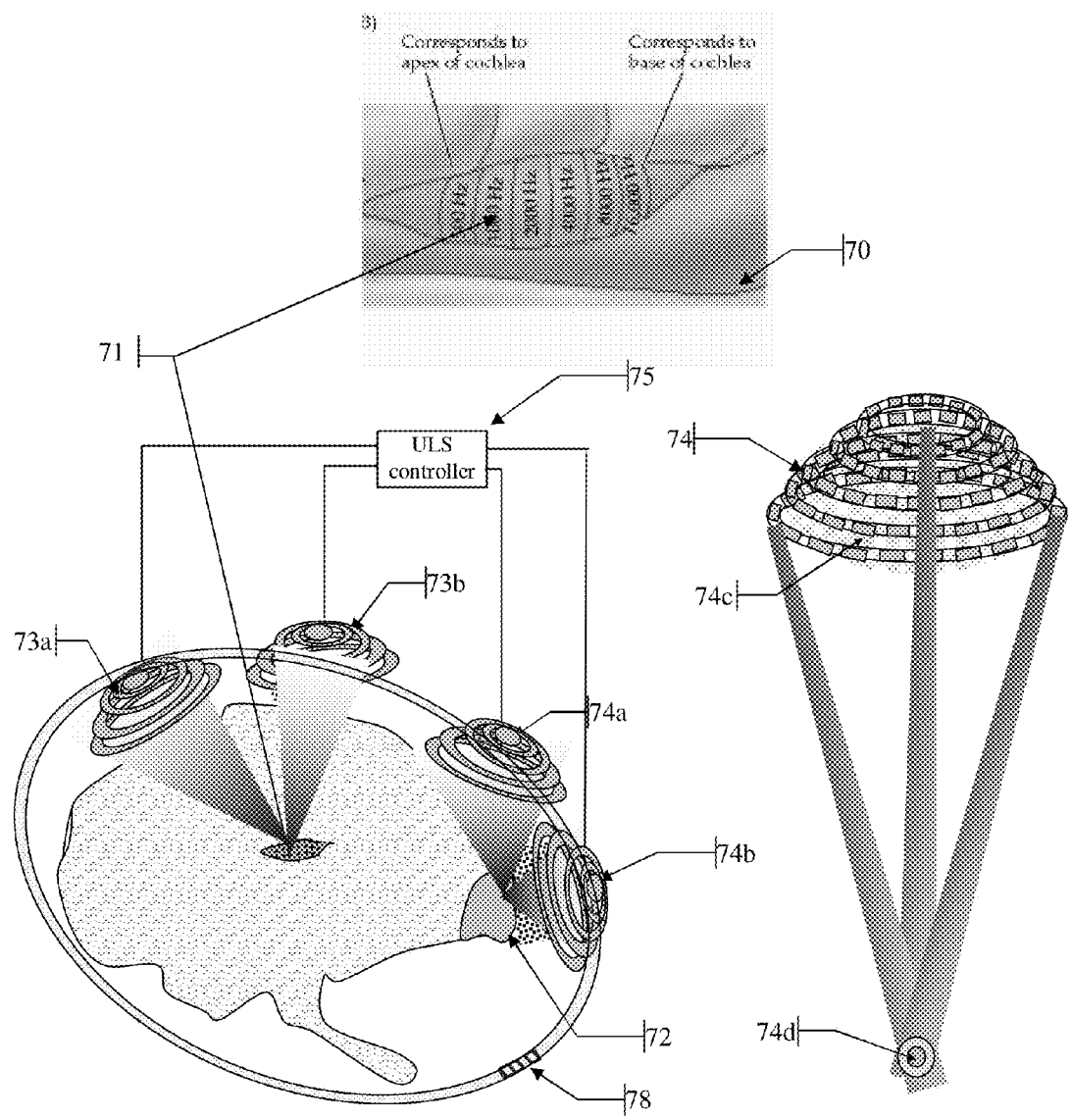
FIG. 7 illustrates the delivery of low intensity focused ultrasound beams to the auditory and visual corteces simultaneously with the delivery of vibrations of the same frequency to the skull and color signals to the eyes.

FIG. 7 illustrates the delivery of low intensity focused ultrasound beams of specific frequency to the brain using concentric circular rings of ultrasound exciters which may be piezoelectric crystals or capacitive MEMS. The concentric rings of exciters 74 form a partial hemisphere filled with a gel 74c having good transmissivity across the crane against which they are pressed. The respective phases of the exciters are tuned so that all the beams reinforce each other at the common focal point 74d.

Two phased arrays of circular rings may be tuned to focus on the same focal point; in such a case the two ultrasound beams will interfere and at their common focal point, and will form ultrasound beams having the sum and difference of the frequencies of the two beams.

This method may be used to excite the A1 of the auditory cortex at the difference frequency 71, for example at 1 kHz if the two beams are tuned at 100 kHz and 101 kHz respectively; another example is to set the two frequencies at 300 kHz and 308 kHz in order to obtain a beam of 8 kHz at the focal point.

To reinforce the pathways between the auditory and visual corteces an ultrasound beam with the same difference frequency may be delivered to the visual 72 and the auditory cortices simultaneously. Moreover both cortices may be excited at the same vibration frequencies delivered by a bone conduction transducers to the crane nearby the cochleas and the frequency of the related color signals delivered to the eyes. The combined intensity of the ultrasound beams at the focal point may be extremely low, of the order of $(1\ W/mm^3)$ and targeted to stimulate only a limited area of the corteces that process said frequencies. The ultrasound beam will stimulate the electrical activity in neurons, by activating both the sodium and calcium channels and may reinforce synaptic transmissions of specific frequencies. The circular phased array transducers may be held in place, pressed against the shaved skull by one or more ratcheted elastic bands 78.

Figure 8:
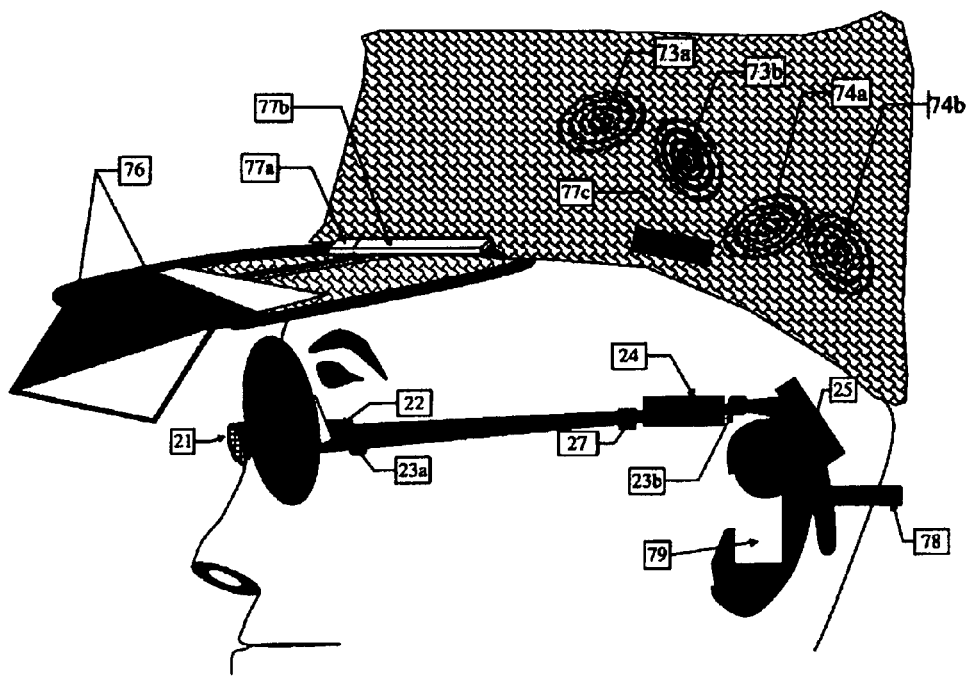
FIG. 8 illustrates a brain training system including a smartphone managed eyeglasses and a cape with a large visor on which is laid a foldable display monitor, an RF transmitter and a battery; the cap also incorporates 4 circular ultrasound emitters with their batteries.

FIG. 8 illustrates the smartphone managed eyeglasses where a foldable display 76 on the visor of a baseball cap displays the images transmitted by the smartphone 80 of the hearing impaired person. In addition to the components embedded in the "hearing eyeglasses" illustrated in FIG. 2, the cap also shows the low intensity ultrasound emitters 73a, 73b, 74a and 74b explained above in connection with FIG. 7 and a $LiPO_4$ battery 77b and 77c that supply power to the display monitor and the ultrasound stimulators.

The eyeglasses may be of the multifocal type, in this case the upper lens having the shorter focus for better viewing the display monitor 76.

Figure 8A:
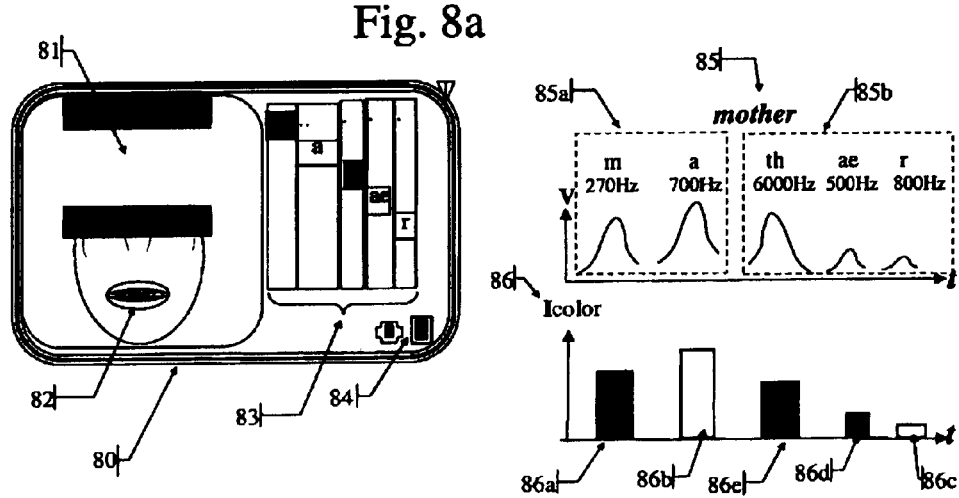
FIG. 8a illustrates a display monitor showing the mouth and lips of a person pronouncing phonemes whose characteristic frequencies are delivered by the BC speaker to the skull of the person and the colors corresponding to said frequencies are simultaneously displayed and/or beamed to the eye of the eyeglasses wearer.

In this training session illustrated in FIG. 8a, the mouth and lips 82 of a person pronouncing the word "mother" 85 are shown, while the face above the mouth is obscured for helping the viewer to concentrate on the movements of the mouth and lips. In parallel with the movement of the mouth and lips saying the word "mother", the syllables [m,a] 85a and [th,ae,r] 85b are displayed sequentially, in time synchronization with the video, with each of the phonemes 86a, 86b, 86c, 86d and 86e are colored 83 according to the one-to-one correspondence scheme with the sound frequencies. The color code is also transmitted to the eye by the LED illuminator 22 to reinforce the link with the other stimulations. In parallel the corresponding vibration frequencies, 270 Hz, 700 Hz, 6000 Hz, 500 Hz and 800 Hz are delivered to the crane by the (BC) transducer(s) explained above in connection with FIG. 5. To better transmit the vibrations, the (BC) transducer mounted on the inside of the "hearing eyeglasses" is pressed against the bone by stretching the band 78 that connects the two temples.

In parallel with the stimulations of the mouth movements, the color signaling and the vibrations transmitted to the crane, the proper locations in the visual and auditory corteces are stimulated by ultrasound waves also of the same frequencies, in order to enhance the pathways between the corteces.

While the training of the plastic brain, in an endeavor to help the damaged auditory organ, makes use of 4 tools in parallel (crane vibrations, ultrasound vibrations, lip reading and color linkage), it is not clear the relative contributions of each of the tools. Some of the suggested tools and techniques will definitely evolve during the training attempts; some will prove to be more useful than the others and probably cross fertilizations will be discovered.

Figure 9:
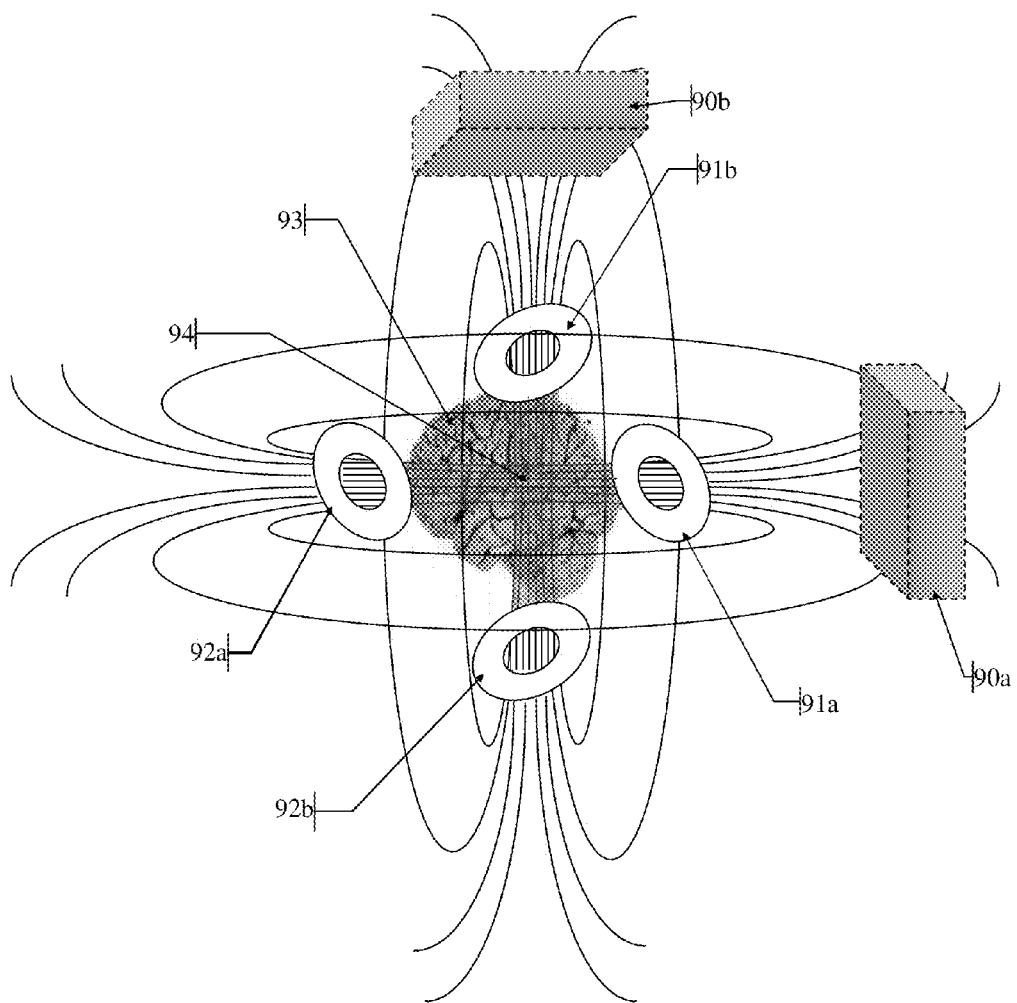
FIG. 9 illustrates the stimulation of the brain with electromagnetic radiation generated between resonant coils.

FIG. 9 illustrates the stimulation of the brain with electromagnetic radiation generated between resonant coils. Inductively coupled resonant coils can transmit magnetic energy with little losses. The figure illustrates two resonant magnetic energy delivery systems perpendicular each to the other. The resonant coils have magnetic cores around which the current carrying wires are wound. The power sources 90a, 90b are coupled to the resonant sources 91a, 91b which are coupled with the distant resonant load coils 92a and 92b. In the illustrated configuration there is no substantial load at the load coils. The only loads are in the near-field due to the impedance of the brain. The coupling factor between the resonant sources 91a, 91b and the resonant loads 92a, 92b may be maximized electronically by adjusting the phase between the resonant coils. In fact the purpose of the illustrated geometry is to keep the magnetic lines from diverging between the resonant coils. In this configuration the magnetic energy will circulate forth and back between the coils with some losses in the intermediate matter, namely the brain depending on the phase between the two coils. In fact changing the phase will determine the energy deposited in the brain along the magnetic lines.

In the illustrated figure the two resonant energy transfer systems are perpendicular each to the other and their magnetic lines cross at a limited region 94, where the deposited energy is cumulative.

Consequently several resonant magnetic energy transfer systems may be placed around the head at the proper angular positions so that their intertwined magnetic lines maximize the energy delivered at this spot. The absolute magnetic energy delivered may be controlled by the phases between the resonant coils.

This method of stimulating selected spots in the brain can be used to stimulate the visual and the auditory corteces simultaneously with the delivery of vibrations to the auditory cortex and the corresponding "color" stimulations to the visual cortex.

There are multiple ways to realize the invention explained above, combine the differentiating features illustrated in the accompanying figures, and devise new embodiments of the methods described, without departing from the scope and spirit of the present invention. Those skilled in the art will recognize that other embodiments and modifications are possible. While the invention has been described with respect to the preferred embodiments thereof, it will be understood by those skilled in the art that changes may be made in the above constructions and in the foregoing sequences of operation without departing substantially from the scope and spirit of the invention. All such changes, combinations, modifications and variations are intended to be included herein within the scope of the present invention, as defined by the claims. It is accordingly intended that all matter contained in the above description or shown in the accompanying figures be interpreted as illustrative rather than in a limiting sense.

We claim:

1. A hearing aid for improved hearing, by replacing each unheard or badly heard audio frequency, by a well heard audio frequency, while the unheard frequencies are multiples or divisions of well-heard frequencies, and,
   training the brain to learn and implement the replacements, wherein,
   said brain training of the hearing impaired person comprises, delivering both to his auditory and visual corteces, images and signals incorporating the original unheard audio frequencies, while he simultaneously hears the corrected audio incorporating the replacement frequencies.

2. A hearing aid for improved hearing, as in claim 1, where the brain training of the hearing impaired person also comprises, simultaneously stimulating the areas of the appropriate neurons of the unheard frequencies, in the auditory and visual cortexes, by delivering to them signals generated by intersecting ultrasound beams.

3. A hearing aid for improved hearing, as in claim 1, where the brain training of the hearing impaired person also comprises, simultaneously stimulating the areas of the appropriate neurons of the unheard frequencies, in the auditory and visual corteces, by delivering to them magnetic signals generated by intersecting magnetic beams generated by inductively coupled resonant coils.

4. A hearing aid for improved hearing, as in claim 1, where the brain training of the hearing impaired person comprises stimulation of the crane bone by vibrations induced by a bone conducting vibrator of single frequencies wherein,
   said vibrator can deliver both the unheard frequencies and well heard frequencies to the inner ear, bypassing the outer ear and the middle ear that may be damaged and wherein,
   said single frequency bone conduction vibrator serves to measure the audiogram of the hearing impaired person and serves to establish a one-to-one correspondence with light frequencies for stimulating the visual cortex.

5. A hearing aid for improved hearing, as in claim 1, wherein
   the brain training of the hearing impaired person comprises a light source of continuous intensity in the visual bandwidth, for establishing a one-to-one correspondence between the visual color bandwidth of blue at 460 nm to red at 620 nm and the audio bandwidth of 250 Hz to 8 kHz at the corresponding loudness and brilliance levels and wherein,
   each and any color between blue and red evoques a specific sound frequency and wherein,
   while the hearing impaired person listens to a frequency corrected audio obtained by replacing the badly heard or unheard frequencies with well heard frequencies, the eye of the hearing impaired person is illuminated by the original colored light source, based on the original badly heard or unheard frequencies, thus forcing the brain to decide between the frequencies of the heard sounds, and the sounds conveyed by the visual cortex that interprets the colors received through the eye according to the original scale.

6. A hearing aid for improved hearing, as in claim 5, wherein the continuous light source of continuous intensity in the visual color bandwidth of blue at 460 nm to red at 620 nm is a bundle of Blue, Green and Red LEDs in a proportion and relative intensity determined by an associated microcontroller.

7. A hearing aid for improved hearing, as in claim 1, wherein
- the brain training of the hearing impaired person comprises a light source calibrated in sound frequencies as in claim 5 and,
- a silent video display that shows the face of a person whose mouth is strongly illuminated, so as to facilitate lip-reading, articulating a word comprising the badly heard or unheard frequencies, and wherein
- a side window in the video display, shows the sequence of the audio frequencies composing the articulated word, where each of the audio frequencies is colored at the corresponding colors as in claim 5, wherein,
- the same word is delivered, to the hearing impaired person's ear corrected by replacing the unheard or badly heard frequencies with well heard frequencies and wherein,
- while the hearing impaired person hears and transmits to the auditory cortex a frequency corrected audio, the visual cortex is illuminated with the original badly heard or unheard frequencies, reinforced by the lip reading imaging of the mouth, thus trumping the version of frequencies reported through the ear.

8. A hearing aid for improved hearing, as in claim 1 wherein,
- the components required for brain training are mounted on eyeglasses temples and a cap with a long visor worn by the hearing impaired person, wherein,
- the system is controlled and managed by a smartphone connected by a bluetooth wireless device to the eyeglasses wherein,
- lip reading of a talking person viewed on the display of the cellphone in a "Face Time" mode, may be transmitted by wireless in real time to the display in front of the eyeglasses and wherein,
- 4 directional microphones at the front and back ends of the temples of the eyeglasses enable to assess the direction of incoming sounds, by setting stringent limits to the time delays of the correlated sounds reaching them, thus rejecting the surrounding noise and wherein,
- bone conducting transducers of our design, able to tailor sound sequences out of single frequencies are mounted at the back of the bows behind the ear, next to the mastoid bone and wherein,
- said bone conducting transducers are pressed against the bone by stretching a band that connects the two temples and wherein,
- a foldable display viewable through the eyeglasses mounted on the visor of a baseball cap worn by the hearing impaired person, shows the images transmitted by the smartphone and wherein,
- the cap also supports the low intensity ultrasound emitters and a $LiPO_4$ battery that supplies power to the display monitor and the ultrasound stimulators.

9. A hearing aid for improved hearing, as in claim 2 wherein,
- said brain trainer comprises pairs of ultrasound emitter phased arrays, where
- said arrays are at a distance of each other, and converge on the same spot within the brain wherein,
- one of the phased array of ultrasound emitters operates at a frequency "f" while the other phased array of ultrasound emitters operates at frequency of "f+$\Delta$f" and wherein,
- an ultrasound radiation of $\Delta f$ frequency is generated at the focal spot of the two beams and wherein,
- different areas of the brain may be stimulated simultaneously at the same or different frequencies by pairs of phased arrays of ultrasound emitters.

10. A hearing aid for improved hearing, as in claim 3 including pairs of resonant coils of magnetic energy emitters placed around the crane wherein,
- said pairs of resonant coils are tuned so as the coupling factor between them is maximized and wherein,
- a phase shift between the energy source coil close to the power source and the load coil at the other side of the crane, determine the magnetic energy dissipated in the brain area between the coils and wherein,
- the positions of pairs of resonant coils with their power sources, positioned around the periphery of the brain determine the intersection area of the magnetic lines where the deposited energy is cumulative and wherein,
- the deposited energy may be increased or decreased by changing the phase between the source coil and the load coil.

11. A hearing aid for improved hearing, as in claim 1 wherein the brain is further trained to start implementing the one-to-one correspondence between colors and substitute frequencies only after instructed to do so following hearing and seeing on the display simultaneously a "start code" and stop implementing the one-to-one correspondence between colors and substitute frequencies after hearing and seeing simultaneously a "stop code", wherein, said start and stop codes are structured as sequences of sound vibrations and corresponding colored signal stimulations to the eye(s).

* * * * *